(12) United States Patent
Schmoll et al.

(10) Patent No.: US 12,386,998 B2
(45) Date of Patent: Aug. 12, 2025

(54) METHOD FOR COUPLING A MEDICAL DEVICE WITH A NETWORK

(71) Applicant: B. Braun Melsungen AG, Melsungen (DE)

(72) Inventors: Horst Schmoll, Guxhagen (DE); Michael Duesterhus, Hessisch Lichtenau (DE)

(73) Assignee: B. Braun Melsungen AG, Melsungen (DE)

( * ) Notice: Subject to any disclaimer, the term of this patent is extended or adjusted under 35 U.S.C. 154(b) by 167 days.

(21) Appl. No.: 17/970,622

(22) Filed: Oct. 21, 2022

(65) Prior Publication Data

US 2023/0131795 A1 Apr. 27, 2023

(30) Foreign Application Priority Data

Oct. 22, 2021 (DE) ...................... 10 2021 127 478.8

(51) Int. Cl.
*G06F 21/62* (2013.01)

(52) U.S. Cl.
CPC ................................ *G06F 21/6245* (2013.01)

(58) Field of Classification Search
CPC ............... G06F 21/6245; H04L 9/3215; H04L 2209/80; H04L 2209/88; H04L 9/40; H04L 2463/061; H04L 63/062; H04L 63/0823; H04L 67/12; H04L 67/55; H04L 63/18; G16H 20/17; G16H 40/67
USPC ........................................................ 726/26
See application file for complete search history.

(56) References Cited

U.S. PATENT DOCUMENTS

| | | | |
|---|---|---|---|
| 7,859,400 B2* | 12/2010 | Urbaszek ............... | G16H 40/67 340/505 |
| 10,955,662 B2* | 3/2021 | Singh .................. | H04W 12/065 |
| 2013/0322348 A1* | 12/2013 | Julian ................ | H04N 21/4384 370/329 |
| 2017/0325091 A1* | 11/2017 | Freeman ................. | H04W 4/90 |
| 2020/0023127 A1 | 1/2020 | Simpson et al. | |
| 2020/0287937 A1 | 9/2020 | Weiler et al. | |
| 2020/0358769 A1* | 11/2020 | Belov .................. | H04L 63/083 |

(Continued)

OTHER PUBLICATIONS

Search Report received in German Application No. 10 2021 127 478.8 dated Jun. 22, 2022, with translation, 12 pages.

(Continued)

*Primary Examiner* — Bryan F Wright
(74) *Attorney, Agent, or Firm* — Christopher A. Rothe; CM Law

(57) ABSTRACT

A system and method for establishing a secure communication connection between at least one medical device and a network. The system includes a first communication channel and at least one second communication channel out of a plurality of second communication channels. The method includes the steps of sending a connection request by the at least one medical device to a control unit, registering the at least one medical device via the first communication channel in the network, and encoding and establishing the communication connection via the at least one second communication channel from the plurality of second communication channels. The at least one second communication channel is selected depending on the data type and/or prioritization of data.

15 Claims, 2 Drawing Sheets

(56) References Cited

U.S. PATENT DOCUMENTS

2021/0050999 A1* 2/2021 Huang .................. H04L 9/14
2021/0083884 A1* 3/2021 Poltorak ............ H04L 63/0428

OTHER PUBLICATIONS

Search Report received in European Application No. 22 202 784.9 dated Mar. 2, 2023, with translation, 15 pages.

* cited by examiner

METHOD FOR COUPLING A MEDICAL DEVICE WITH A NETWORK

CROSS-REFERENCE TO RELATED APPLICATION(S)

This application claims priority under 35 U.S.C. § 119 to German Application No. 10 2021 127 478.8, filed Oct. 22, 2021, the content of which is incorporated by reference herein in its entirety.

FIELD

The present disclosure relates to a method for establishing a secure and trustworthy communication connection between at least one medical device, in particular an infusion pump, and a network.

BACKGROUND

The disclosure focuses on secure coupling/connection of devices, in particular medical devices, in particular infusion pumps with a clinical IT platform/a clinical server/a network. Establishing a trusted connection/communication connection is used to prove authenticity, confidentiality, and integrity between at least one medical device and a clinical IT platform/network within an untrusted hospital network.

In current modern implementations, coupling/connecting is usually initially based on the manual exchange of security verification. Known standards are based, for example, on verifications such as Simple Certificate Enrollment Protocol (SCEP) or Enrollment over Secure Transport (EST).

Current solutions require a preconfigured authenticity between the at least one medical device and the server/network, for example through already defined, trustworthy certificates. These certificates are downloaded and thus the data traffic is encoded.

SUMMARY

Against this background, the object of the present disclosure is to eliminate or at least reduce the disadvantages of the prior art. Accordingly, one objective of the present disclosure is to solve the following problems:
  Proving the relationship between the digital identity and the physical identity of the at least one medical device;
  Enabling encoding for (asynchronous) messages with unknown recipients;
  Verifying the integrity and authenticity of messages;
  Lockout of unknown/untrusted devices; and
  Immediate revocation of the trust relationship at any time.

The object is solved by a method for establishing a secure and trustworthy communication connection between at least one medical device, in particular at least one infusion pump, and a network. In the following, a 'client' is to be understood as at least one medical device.

The secure and trustworthy communication connection between at least one medical device and a network is established with a first communication channel and at least one second communication channel out of a plurality of second communication channels, comprising the following steps. In a first step, a connection/coupling request is sent by the at least one medical device to a control unit. In a subsequent step, the at least one medical device is registered in the network via the first communication channel. In a final step, the communication connection is encoded and established via the at least one second communication channel from the plurality of second communication channels, wherein the at least one second communication channel is selected depending on the data type and/or prioritization of data.

In other words, a known 'access secret' is exchanged during the installation/connection/coupling of the at least one medical device and of the IT system/network. At the at least one medical device, the operator/user starts the coupling/pairing sequence by requesting the coupling/connection via a preferably secured, first communication channel. After an optional confirmation of the pairing request by the IT system operator, the system sets up dedicated second communication channels for the at least one medical device. The system generates certificates and distributes the certificate over the dedicated communication channels. At the end of the coupling/pairing process, the communication channels between the device and the IT system are protected by the generated security certificates.

Such a coupling process has the advantage that several medical devices can use the same first communication channel already for the registration step and that multiple use of different medical devices is also possible with regard to the second communication channels. In this way, a large number of communication channels can be saved.

In other words, the connection/coupling process for a new medical device can be described by the following stages. When a new medical device joins the network, the at least one medical device has to send a pairing/connection/coupling request to the control unit. Once a control unit application receives a request, the operator/user has the option to accept or reject the connection request in order for the at least one medical device to join the network.

Before the connection/coupling process is initiated, the at least one medical device has to be configured to connect to the network on site. In addition, the at least one medical device has to be configured with the IT address of a message broker. The message broker is understood to be a communication system that can run on multiple, distributed servers that share data traffic among each other and support fail-safe operation. In this communication system, information is provided with a time stamp and stored in so-called topics. The stored information is replicated and distributed in the message broker and is available to server applications for further processing.

Further embodiments are described below.

It is preferred if the first communication channel is a registration channel and the registration is a one-time method step per medical device, wherein in the method step of the registration, the at least one medical device is configured for the communication connection via a verification step. Here, the control unit runs on a server connected to the network.

It is advantageous if in the verification step, the control unit specifies a connection mode, which in particular includes an optical verification, a manual verification or a simple connection without verification.

In other words, there are three different modes for pairing/coupling/connecting at least one medical device with the clinical network. A first mode is optical verification. Here, a mobile terminal device is additionally required to scan a QR code and to read out information contained therein. A second mode is manual verification, and a third mode is simple coupling/connecting, where no verification is required and has a reduced trust level. The third mode is only to be used in a secured network environment. In manual verification, the at least one medical device shows a key confirmation code encoded in a display and the operator/user can confirm this at the control unit, whereupon the control unit sends further commands.

The selection of which of the three verification modes is used is entirely controlled by an application of the control unit. An application on the side of the at least one medical device would always use the simple coupling/connecting according to the third mode, since this is executed in a trustworthy network environment. That is, the simple coupling/connecting is a first expansion stage, which is expanded into a two-factor authentication by optical or manual verification.

The following requirements exist for connecting/coupling the at least one medical device:
- the at least one medical device has to be configured to connect to the network,
- the at least one medical device has to know the address of the message broker, wherein preferably the use of a predefined dns entry is to be used as fallback,
- the at least one medical device has to know the access secret/the key (hospital access secret),
- optionally, the at least one medical device may have a trustworthy root certificate (CertCA).

It is preferred if multiple use of a key for multiple medical devices is provided in the method step of encoding.

It is advantageous if the plurality of second communication channels are provided and configured to provide different keys in each case, wherein the different keys fulfill different criteria, in particular security criteria, depending on the data type and/or prioritization of the data.

It is advantageous if in the encoding step, the control unit confirms the establishment of the communication connection, wherein the communication connection is encoded with a network key and a network key ID.

It is preferred if the at least one medical device receives the network key and the network key ID and stores them in a persistent memory.

It is advantageous if the key of the at least one second communication channel is known to the at least one medical device.

In other words, the method can also be divided into the following five steps:

In a first step, the at least one medical device enters a connection/coupling mode. This can be done automatically depending on certain criteria or can be initiated manually from a user interface of the at least one medical device. The at least one medical device generates its own static EC-key pair and stores it in the persistent local memory. A static EC-key pair (an elliptic curve key) is initially generated by the at least one medical device. The control unit derives a transient (ephemeral) key pair from this.

The at least one medical device establishes a TLS connection to the broker/intermediary using a certificate. If no trustworthy root certificate is available, the at least one medical device has to disable the TLS certificate validation. TLS (Transport Layer Security) is also known by its predecessor name Secure Sockets Layer (SSL) and is an encoding protocol for secure data transmission on the Internet. The at least one medical device sends a connection/coupling/pairing request to a first topic 'ais.register.<client>' and uses the following access secret/the key for encoding:
- a live load (data to be transmitted) contains a certification signing request for the EC-key pair of the at least one medical device;
- the live load contains information of the at least one medical device for display at the control unit;

identifier, device type, family, serial number, firmware version, etc.; and
- the live load connection status field issues a connection request.

In a second step, the at least one medical device attempts to subscribe to (that is, receive messages from) a second topic 'ais.<client>.<client_identifier>' from the message broker, the provisioning of which in the message broker is initiated by the control unit as described below.

The control unit consumes messages from the first topic and displays a list of the medical devices that have requested a connection/pairing/coupling. The operator/user has the choice of accepting or rejecting the request. If the operator accepts the demand/request, the control unit creates a temporary ephemeral EC-key pair. The control unit creates the second topic 'ais.<client>.<client_identifier>' and sets the appropriate access-control levels for the identity of the certificates. The control unit forwards the certification signing request for the EC-key pair of the at least one medical device to the internal infrastructure and receives the signed certificate. The control unit adds the appropriate access-control levels for the identity of the corresponding certificate to a third topic 'ais.command.<client>'. The control unit generates a connection/coupling command or a response to the medical device on the second topic using the access secret/the keys for encoding. Here, the live load contains the temporary, ephemeral public key of the control unit, the signed certificate of the medical device, and the security certificate. In addition, the connection/coupling/pairing status field of the live load contains the options for optical verification, manual verification, or simple verification.

In a third step, the at least one medical device consumes the command for verification from the second topic. The at least one medical device and the control unit can now compute a shared secret 'z' for key generation. The at least one medical device stores the received, signed certificate and uses it to renew the TLS connection. The at least one medical device generates a key confirmation. Depending on the pairing/coupling/connection mode, this key confirmation is transmitted with the 'PAIRING-VERIFIED' command to the third topic for encoding:
 a. In case of simple coupling/connecting, the at least one medical device sends the order/command (PAIRING_SIMPLE) of the verification type itself
 b. In the case of manual coupling/connecting, the at least one medical device shows the key confirmation code in code on the display, and the operator/user can confirm on the control unit that the confirmation is correct. The control unit then sends the command (PAIRING_CODE).
 c. In the case of optical coupling/connecting, the at least one medical device shows the key confirmation code as a QR code on the display, and the operator/user can send it to the control unit with a mobile terminal device via a second secure communication channel, whereby the control unit sends the command.

The control unit checks whether the key confirmation code is identical.

In a fourth step, the control unit changes the access-control levels for the second topic and removes the identity of the corresponding certificate. The control unit sends a PAIRING_CONFIRMED order/command to the second topic and uses the secret 'z' for encoding. The live load contains the network key and the network key ID for further encoding. The at least one medical device receives the PAIRING_CONFIRMED command/order and stores the received network key and network key ID in the persistent memory.

In a fifth step, the at least one medical device sends a PAIRING_FINISHED order/command to the third topic and uses the network key for encoding. The at least one medical device indicates 'connection successful'. The control unit adds the appropriate access-control levels for the identity from the security certificate to the other common topics. The control unit publishes a message to the topic of the fourth topic 'ais.meta.<client>' with the security certificate. The at least one medical device connects to the corresponding topics and starts producing data for the network.

Furthermore, the present disclosure relates to a communication system for providing a secure and trustworthy communication connection between at least one medical device and a network, comprising the at least one medical device, in particular an infusion pump, the network, a control unit which is provided to receive a coupling request of the at least one medical device, a first communication channel configured and provided for registering the at least one medical device in the network, and at least one second communication channel of a plurality of second communication channels configured and provided for encoding the communication connection, wherein at least one of the plurality of second communication channels is selectable depending on data type and/or prioritization of data.

It is preferred if the communication system is provided and configured to perform and/or carry out the method according to one of the preceding aspects.

DETAILED DESCRIPTION

The following describes configuration examples of the present disclosure based on the accompanying figures.

Figure 1:
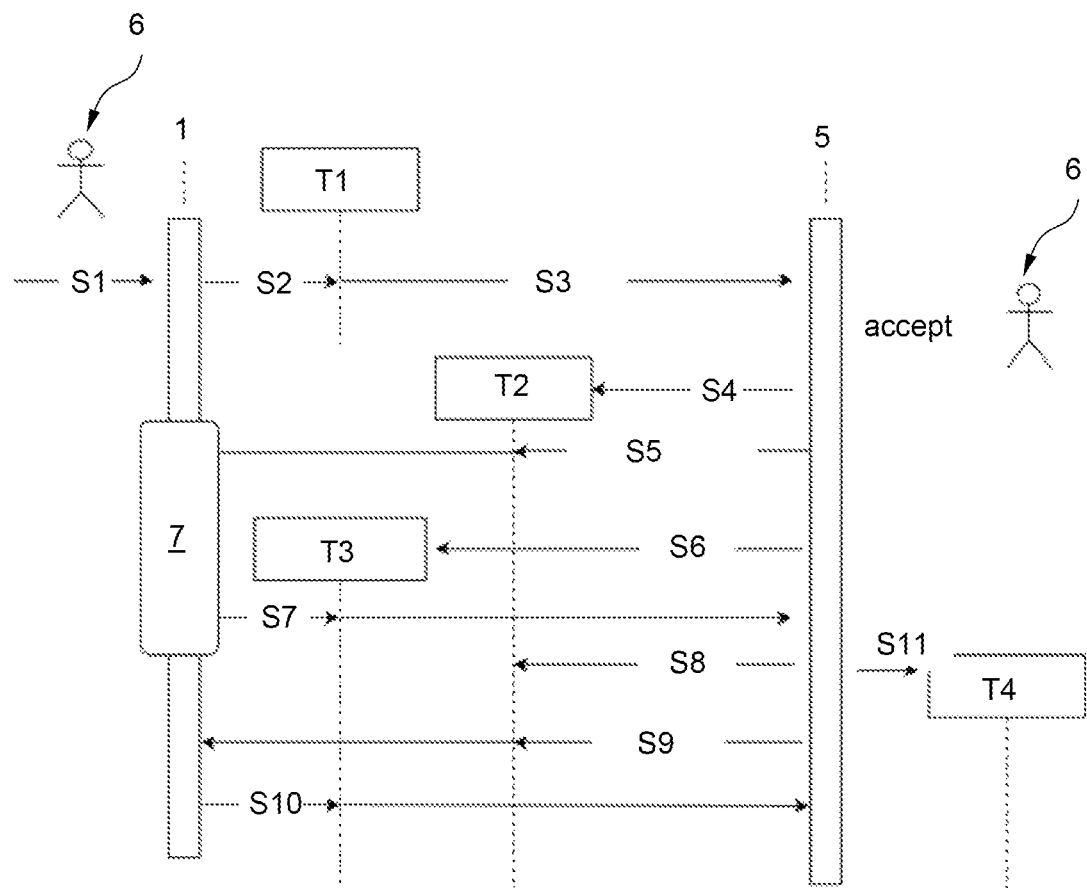
FIG. 1 is a representation illustrating a connection/coupling establishment according to the present disclosure.

FIG. 1 is a representation illustrating a secure and trustworthy connection/coupling establishment according to the present disclosure. In a first step S1, a connection/coupling is initiated by at least one medical device 1 via a user 6 or automatically. Here, a connection request is sent by the at least one medical device 1 to a control unit 5 according to a second step S2. In particular, a connection request according to S2 is sent to a topic T1 'ais.register.<client>' and an access secret/a key is used for encoding. In a further step S3 the connection request is processed. Here, the control unit 5 processes messages from topic T1 and displays a list of medical devices 1 that have requested pairing/connection/coupling according to S2. The user 6 can decide to accept or reject the connection request.

In a step S4, the control unit creates a Topic T2 'ais.<client>.<client_identifier>', wherein the at least one medical device 1 periodically attempts to subscribe to Topic 2 until it is created. The control unit 5 generates a temporary ephemeral EC-key pair and, provided the user 6 has accepted the connection request, the control unit 5 sets the corresponding access-control levels at Topic T2 for the identity of corresponding certificates. Meanwhile, a display of the at least one medical device indicates that the connection/coupling is in progress.

In a fifth step S5, after the connection/coupling is approved/recognized, the control unit 5 generates a coupling command to the at least one medical device 1 of topic T2 using a key/access secret for encoding. The at least one medical device 1 is now in a coupling/connection mode and processes a command from topic T2. The command from topic 2 indicates the type of verification. One of the three commands can be selected: 'pairing_qrcode', 'pairing_code' or 'pairing:simple'. The at least one medical device 1 and the control unit 5 can now calculate a common secret 'z'.

The control unit 5 forwards at least one certification signing request for the EC-key pair of the at least one medical device 1 to an internal certification infrastructure and receives a signed certificate. In a step S6, the control unit 5 adds corresponding access-control levels for the identity of the certificates to a topic T3 'ais.command.<client>'. Depending on the connection/coupling mode, a key confirmation with the command 'connection verified' is transmitted to the topic T3 with the secret 'z' for encoding according to a step S7.

Provided that the key confirmation has been checked by the control unit 5, the control unit 5 changes the access-control levels for the topic 2 according to step S8 and removes the corresponding identities of the corresponding certificate. In a step S9, the control unit 5 sends a 'connection confirmed' command to the topic T2 and uses the secret 'z' for encoding. Thereupon, a live load, that is, the communication data between the at least one medical device 1 and the control unit 5, has a platform key and a platform key ID for further encoding. The at least one medical device 1 receives the command 'connection confirmed' and stores the received platform key and platform key ID in a persistent/non-volatile memory.

In a penultimate step S10, the at least one medical device 1 sends a 'connection completed' command to the topic T3 and uses the platform key for encoding. Here, the at least one medical device 1 indicates 'connection successful'. The control unit 5 adds corresponding access-control levels for the identity of the certificate to a fourth topic T4 'ais.meta.<client>' and the control unit 5 publishes a message to the topic 4 with the corresponding certificate. Thereupon, the communication connection between the at least one medical device 1 and the network 2 is established.

Figure 2:
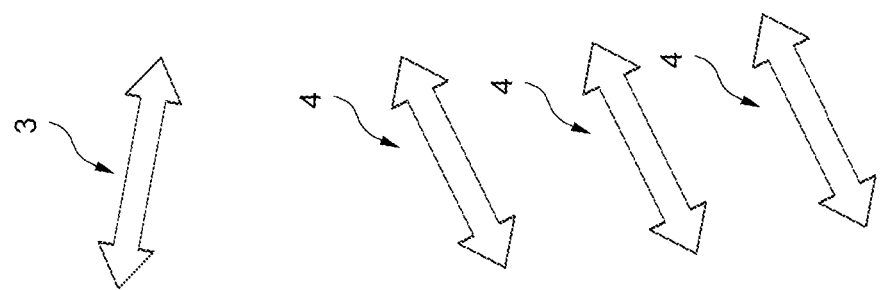
FIG. 2 is a representation illustrating a communication system according to the present disclosure.
Figure 2:
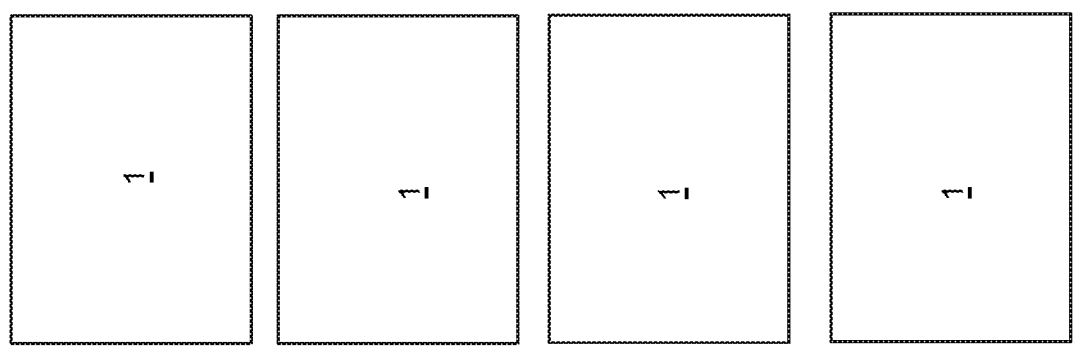
Figure 2:
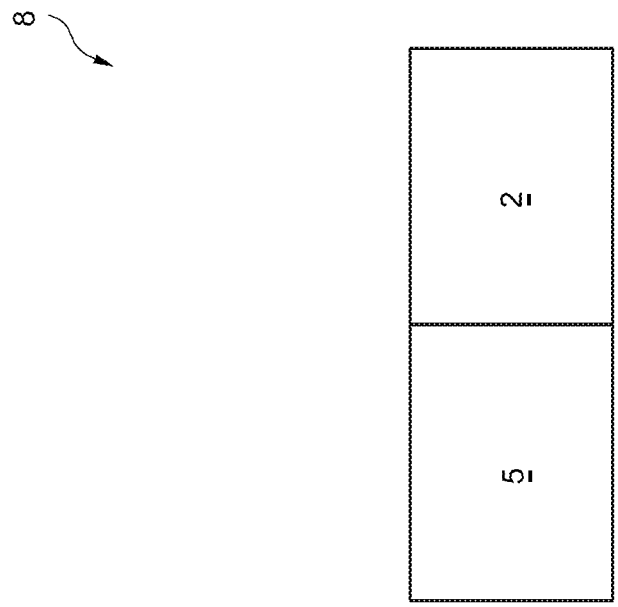

FIG. 2 is a representation illustrating a communication system 8 according to the present disclosure. Here, four medical devices 1 are shown as examples. Each of the medical devices 1 shown can perform the registration step according to S4 to S7 via a first communication channel 3. Furthermore, three second communication channels 4 are shown by way of example in FIG. 2. Each of the medical devices 1 shown is configured and provided to establish an encoded communication channel to a network 2 via at least one of the second communication channels 4 shown. The selection of the second communication channel 4 is made by a control unit 5 depending on the data/information to be transmitted.

The invention claimed is:

1. A method for establishing a secure and trustworthy communication connection between at least one medical device and a network, having a first communication channel and at least one second communication channel, the method comprising:
   sending a connection request by the at least one medical device to a control unit connected to the network;
   registering the at least one medical device via the first communication channel in the network; and encoding and establishing the communication connection via the at least one second communication channel, wherein the at least one second communication channel is selected depending on a data type and/or a prioritization of data;

wherein the first communication channel is a registration channel and the registering step is a one-time method step per medical device, wherein in the registering step, the at least one medical device is configured for the communication connection via a verification step; and in the verification step, the control unit selects a connection mode, wherein, to select the connection mode, the control unit is configured to operate by:
  considering the connection mode by evaluating each of a plurality of candidates comprising a no verification mode and at least one of: an optical verification mode, and a manual verification mode,
  upon determining that the medical device and the network are communicating by a secured network environment, selecting the no verification mode, and
  upon determining that the medical device and the network are communicating via an untrusted network, selecting the optical verification mode or the manual verification mode.

2. The method according to claim 1, wherein multiple use of a key for multiple medical devices is provided in the method step of encoding.

3. The method according to claim 1, wherein the at least one second communication channel comprises a plurality of second communication channels configured to provide a plurality of keys, each key being different, wherein the keys fulfil different criteria depending on the data type and/or prioritization of the data.

4. The method according to claim 1, wherein in the encoding step, the control unit confirms the establishment of the communication connection, wherein the communication connection is encoded with a network key and a network key ID.

5. The method according to claim 4, wherein the at least one medical device receives the network key and the network key ID and stores the network key and the network key ID in a persistent memory.

6. The method according to claim 1, wherein the at least one second communication channel is configured to provide a key that is known to the at least one medical device.

7. A communication system for providing a communication connection between at least one medical device and a network, the communication system comprising:
  the at least one medical device;
  the network;
  a control unit configured to receive a connection request of the at least one medical device and perform a verification step;
  a first communication channel configured for registering the at least one medical device in the network; and
  at least one second communication channel configured to encode said communication connection,
  the at least one second communication channel being selectable depending on a data type and/or prioritization of data;
  wherein, to perform the verification step, the control unit is configured to select a connection mode by:
    considering the connection mode by evaluating each of a plurality of candidates comprising a no verification mode and at least one of: an optical verification mode, and a manual verification mode;
    upon determining that the at least one medical device and the network are communicating by a secured network environment, selecting the no verification mode, and
    upon determining that the at least one medical device and the network are communicating via an untrusted network, selecting the optical verification mode or the manual verification mode.

8. The method according to claim 1, wherein the plurality of candidates comprising all three of: the verification mode, the manual verification mode, and the no verification mode.

9. The communication system according to claim 7, wherein the plurality of candidates comprises all three of: the optical verification mode, the manual verification mode, and the no verification mode.

10. The method according to claim 1, wherein the optical verification mode comprises operating a mobile terminal to scan a QR code and to read out information contained in the QR code.

11. The method according to claim 10, wherein the QR code is shown on a display of the medical device.

12. The method according to claim 1, wherein the manual verification mode comprises displaying a confirmation code on a display of the medical device.

13. The communication system according to claim 7, wherein the optical verification mode comprises operating a mobile terminal to scan a QR code and to read out information contained in the QR code.

14. The communication system according to claim 13, wherein the QR code is shown on a display of the at least one medical device.

15. The communication system according to claim 7, wherein the manual verification mode comprises displaying a confirmation code on a display of the at least one medical device.

* * * * *